US012773140B2

(12) United States Patent
Belle et al.

(10) Patent No.: US 12,773,140 B2
(45) Date of Patent: Oct. 27, 2026

(54) STABLE REFERENCE FOR SENSOR APPARATUS

(71) Applicant: Medtronic, Inc., Minneapolis, MN (US)

(72) Inventors: Anna M. Belle, Scottsdale, AZ (US); Mohsen Askarinya, Chandler, AZ (US); Omid Mahdavi, Tucson, AZ (US); Luling Wang, Mason, OH (US)

(73) Assignee: Medtronic, Inc., Minneapolis, MN (US)

( * ) Notice: Subject to any disclaimer, the term of this patent is extended or adjusted under 35 U.S.C. 154(b) by 1019 days.

(21) Appl. No.: 17/964,863

(22) Filed: Oct. 12, 2022

(65) Prior Publication Data

US 2024/0122505 A1 Apr. 18, 2024

(51) Int. Cl.
*A61B 5/145* (2006.01)
*A61B 5/1486* (2006.01)

(52) U.S. Cl.
CPC ...... *A61B 5/14546* (2013.01); *A61B 5/14865* (2013.01)

(58) Field of Classification Search
CPC . A61B 5/14546; A61B 5/14865; A61B 5/145; G01N 33/48707; G01N 27/3274
See application file for complete search history.

(56) References Cited

U.S. PATENT DOCUMENTS 5,112,455 A 5/1992 Cozzette et al.
2007/0163894 A1* 7/2007 Wang .................. A61B 5/1473 205/792
2014/0018653 A1* 1/2014 Staib .................. G01N 27/3272 600/347
2019/0178830 A1 6/2019 Wilhelm et al.
2020/0000386 A1* 1/2020 Gupta .................. A61B 5/1495

FOREIGN PATENT DOCUMENTS

EP 1219958 7/2002
EP 1219958 A1 * 7/2002 ......... G01N 27/4165
EP 1219959 7/2002
EP 3859322 8/2021
WO 2009/055274 4/2009

OTHER PUBLICATIONS

International Search Report and Written Opinion for PCT/IB2023/059865 dated Nov. 13, 2023 (13 pages).

* cited by examiner

*Primary Examiner* — Christian Jang
(74) *Attorney, Agent, or Firm* — Mueting Raasch Group

(57) ABSTRACT

An analyte sensor apparatus for detecting an analyte in a target environment includes a plurality of electrodes and a controller. The plurality of electrodes may be configured to provide a plurality of electrode signals based on a target environment. The plurality of electrodes may include one or more working electrodes, a first reference electrode, and a second reference electrode. The one or more working electrodes may be configured to provide an analyte signal based on a presence of an analyte in the target environment. The first reference electrode may be configured to provide a first baseline signal of the target environment. The second reference electrode may include a different type of electrode than the first reference electrode. The second reference electrode may be configured to provide a second baseline signal of the target environment. The controller may be operatively coupled to the plurality of electrodes.

19 Claims, 5 Drawing Sheets

STABLE REFERENCE FOR SENSOR APPARATUS

FIELD

The present disclosure relates to, among other things, analyte sensors.

TECHNICAL BACKGROUND

Analyte sensors may be used in a wide range of applications such as, for example, point-of-care monitoring, environmental monitoring, food control, drug discovery, forensics, biomedical research, etc. Analyte sensors may be used to detect a substance of interest (e.g., an analyte) in a target environment. Analyte sensors generally include biotransducers (e.g., electrodes) to provide signals that can be used to determine the presence of an analyte in the target environment. Such biotransducers may be subject to noise in the target environment, sensor drift, reference variation, or other effects that can impact sensor response and accuracy.

To ensure accurate sensing of an analyte in a target environment, analyte sensors may be periodically calibrated or replaced. However, in some applications, calibration or replacement of the analyte sensors may be burdensome and expensive.

BRIEF SUMMARY

As described herein, accurate and reliable analyte sensing can be achieved using analyte sensors that include at least two references electrodes that are each a different type of electrode. Generally, analyte sensors include at least one reference electrode to provide a reference signal and one working electrode to provide an analyte signal used together to determine the presence of an analyte in a target area. However, the reference electrode may be subject to variation, noise, drift, and other effects that can negatively impact the accuracy of analyte sensors. To correct for such effects, a second reference electrode that is a different type of electrode than the first reference electrode can be used to correct for drift and variation of the first reference electrode and/or to filter noise. Additionally, the use of two reference electrodes can allow for analyte sensing to continue even if one of the reference electrodes fails or otherwise stops providing reliable signals. Accordingly, apparatus, systems, and methods that use two different reference electrodes may provide more accurate and reliable analyte sensing.

Described herein, among other things, is analyte sensor apparatus for detecting an analyte in a target environment comprising a plurality of electrodes to provide a plurality of electrode signals based on a target environment and a controller. The plurality of electrodes comprises one or more working electrodes, a first reference electrode, and a second reference electrode. The one or more working electrodes are configured to provide an analyte signal based on a presence of an analyte in the target environment. The first reference electrode is configured to provide a first baseline signal of the target environment. The second reference electrode comprises a different type of electrode than the first reference electrode. Additionally, the second reference electrode is configured to provide a second baseline signal of the target environment. The controller is operatively coupled to the plurality of electrodes and is configured to receive the plurality of electrode signals and provide one or more sensor signals based on the received plurality of electrode signals.

The plurality of electrode signals comprises the analyte signal, the first baseline signal, and the second baseline signal.

In general, in one aspect, the present disclosure describes an analyte sensing system comprising a sensor apparatus to provide one or more sensor signals based on a plurality of electrode signals and a computing apparatus. The sensor apparatus comprises a plurality of electrodes to provide the plurality of electrode signals based on a target environment. The plurality of electrodes comprises one or more working electrodes, a first reference electrode, and a second reference electrode. The one or more working electrodes are configured to provide an analyte signal based on a presence of an analyte in the target environment. The first reference electrode is configured to provide a first baseline signal of the target environment. The second reference electrode comprises a different type of electrode than the first reference electrode. The second reference electrode is configured to provide a second baseline signal of the target environment. The plurality of electrode signals comprises the analyte signal, the first baseline signal, and the second baseline signal. The computing apparatus comprises one or more processors and is operatively coupled to the sensor apparatus. The computing apparatus is configured to receive the one or more sensor signals and provide an analyte level of the target environment based on the one or more sensor signals In general, in another aspect, the present disclosure describes a method for detecting an analyte in a target environment. The method comprises receiving a plurality of electrode signals. The plurality of electrode signals comprises one or more analyte signals of the target environment from one or more working electrodes disposed in the target environment, a first baseline signal of the target environment from a first reference electrode, and a second baseline signal of the target environment from a second electrode, the second electrode comprising a different type of electrode than the first electrode. The method further comprises providing an analyte level of the target environment based on the plurality of electrode signals.

Advantages and additional features of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative and are not intended to limit the scope of the claims in any manner.

BRIEF DESCRIPTION OF THE DRAWINGS

The following detailed description of specific embodiments of the present disclosure can be best understood when read in conjunction with the following drawings, in which.

The schematic drawings are not necessarily to scale.

DETAILED DESCRIPTION

Reference will now be made in greater detail to various embodiments of the subject matter of the present disclosure, some embodiments of which are illustrated in the accompanying drawings. Like numbers used in the figures refer to like components and steps. However, it will be understood that the use of a number to refer to a component in a given figure is not intended to limit the component in another figure labeled with the same number. In addition, the use of different numbers to refer to components in different figures is not intended to indicate that the different numbered components cannot be the same or similar to other numbered components.

Accurate and reliable analyte sensing can be achieved using analyte sensors and/or systems that include two different reference electrodes as described herein. The use of two different reference electrodes may allow the natural drift of reference electrodes to be accounted for such that accurate analyte levels may be provided without frequent and potentially cumbersome recalibration of sensor apparatus. Additionally, noise that may distort a baseline signal can be filtered out and reference electrode variation can be corrected. Accordingly, apparatus, systems, and methods that use two different reference electrodes as described herein may provide more accurate and reliable analyte sensing.

Figure 1:
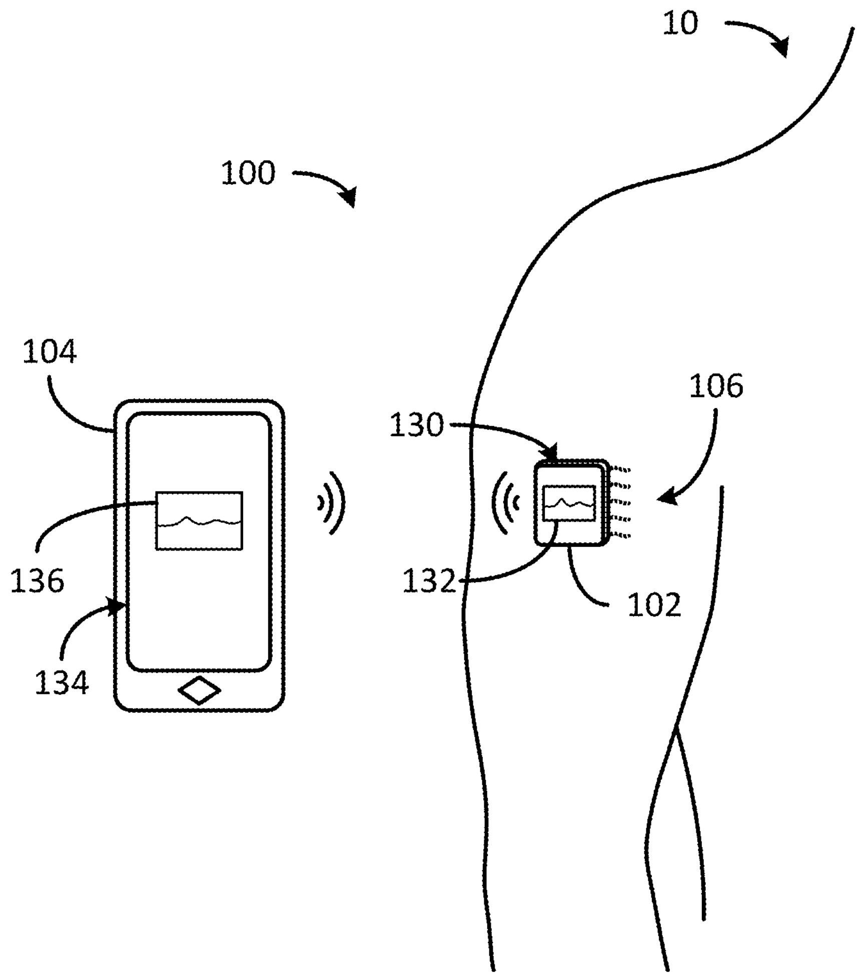
FIG. 1 is a schematic diagram of an embodiment of an analyte sensing system.
Figure 2:
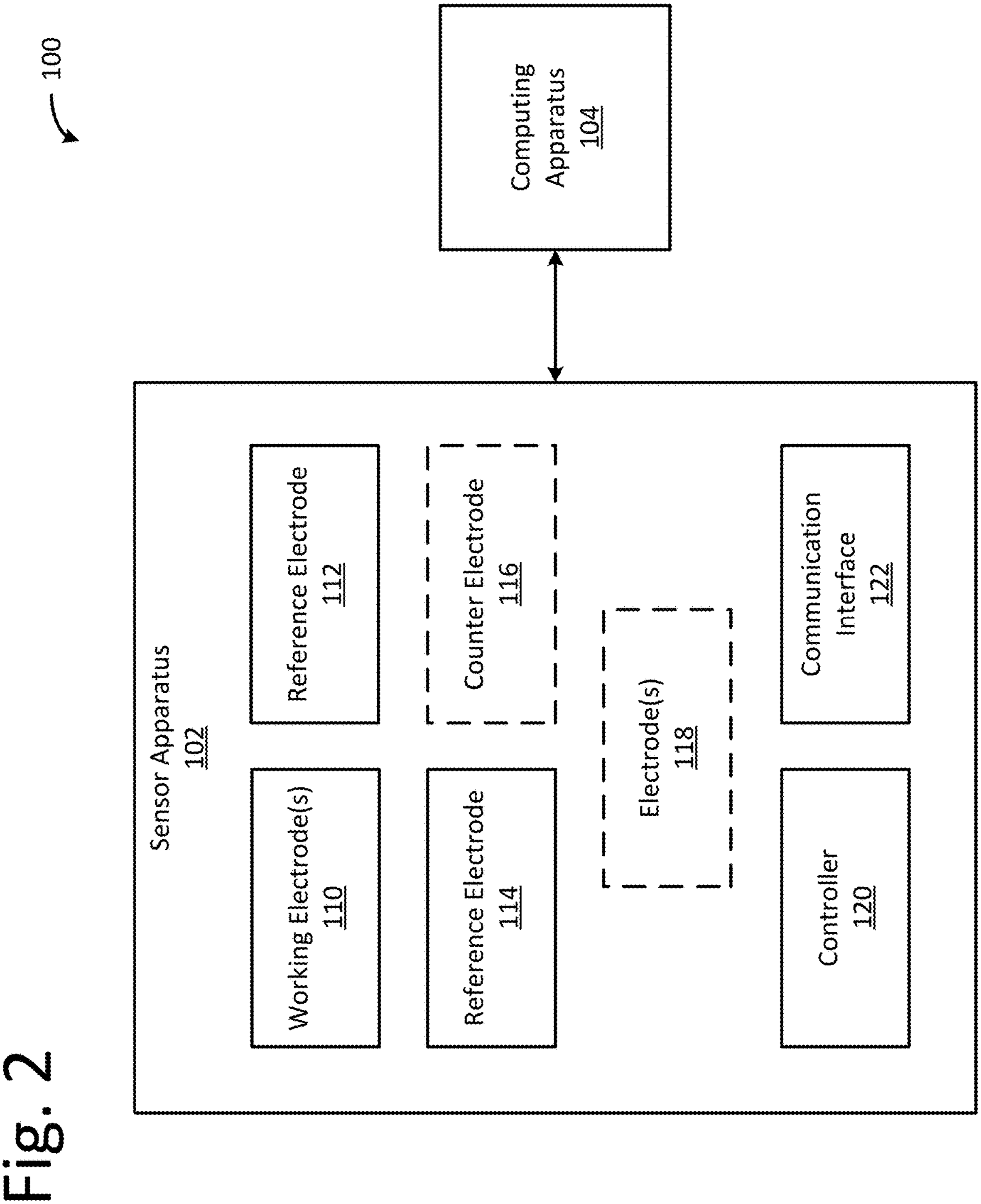
FIG. 2 is a schematic block diagram of the analyte sensing system of FIG. 1.

An analyte sensing system is depicted in FIGS. 1 and 2. FIG. 1 shows schematic diagram of an analyte sensing system 100 including an analyte sensor apparatus 102 and a computing apparatus 104 during use. FIG. 2 shows a schematic block diagram of the analyte sensing system 100.

The analyte sensing system 100 includes the analyte sensor apparatus 102 for detecting analyte in a target environment 10. As shown, the target environment 10 is a person or patient. However, the target environment 10 may include any environment where detection of analyte levels or concentrations may be desired. For example, the analyte sensor apparatus 102 may be used to detect analytes that may include reagents in chemical processes, pollutants (e.g., atmospheric or aquatic), health markers (e.g., cholesterol, triglycerides, iron, vitamins, etc.), any substance of a comprehensive metabolic panel (e.g., substances in blood including glucose, calcium, sodium, potassium, carbon dioxide, chloride, albumin, total protein, alkaline phosphatase, alanine transaminase, aspartate aminotransferase, bilirubin, blood urea nitrogen, and creatinine), etc. Accordingly, the target environment 10 may include, for example, a manufacturing facility, a body of water, a particular geographical area, a patient, human samples (e.g., blood, urine, saliva, etc.), environmental samples (e.g., air, water, soil, vegetation), cell cultures, food samples, etc. Furthermore, the analyte sensor apparatus 102 may be an implantable medical device, a remote sensor, a wearable device, hospital equipment, lab equipment, etc.

The analyte sensor apparatus 102 includes a plurality of electrodes 106. Each of the plurality of electrodes 106 may be configured to provide signals based on the target environment 10 that can be used to determine an analyte level or analyte concentration in the target environment 10. Each of the plurality of electrodes 106 may provide an electrical interface between the analyte sensor apparatus and the target environment. Signals provided by the plurality of electrodes 106 may include baseline signals, analyte signals, error condition signals, or other signals that can be used to determine an analyte level in the target environment.

The plurality of electrodes 106 may include any suitable type of electrode to provide an electrical interface, act as an electrochemical biotransducer, and/or be part of an electronic biotransducer. Electrodes may include a biorecognition element that selectively reacts with a target analyte and produces an electrical signal that is proportional to the analyte concentration. Electrodes may be used in amperometric or potentiometric sensor apparatus.

Amperometric sensor apparatus may be used to detect a change in current as a result of electrochemical oxidation or reduction. Typically, a bioreceptor molecule is immobilized on one or more working electrodes (e.g., gold, carbon, platinum, etc.). A potential applied between the one or more working electrodes and a reference electrode (e.g., silver/silver-chloride) may be fixed at a given value while the current is measured with respect to time. The applied potential may be the driving force for an electron transfer reaction. The current produced as a result of the applied potential may be a direct measure of the rate of electron transfer. Accordingly, the measured current may reflect the reaction occurring between the bioreceptor molecule and the analyte where the current is limited by the mass transport rate of the analyte to the electrode.

Potentiometric sensor apparatus may be used to measure a potential or charge accumulation. Biotransducers used for potentiometric sensing may include one or more working electrodes (e.g., an ion selective electrode) and a reference electrode. Each of the one or more working electrodes may include a membrane or surface that selectively interacts with a charged ion of interest (e.g., the analyte), causing the accumulation of a charge potential on each of the one or more working electrodes when compared to the reference electrode. The reference electrode may provide a constant half-cell potential that is unaffected by analyte concentration. A voltmeter may be used to measure the potential between the each of the one or more working electrodes and the reference electrode when no significant current flows between them. The potentiometric response may be governed by the Nernst equation such that the measured potential is proportional to a logarithm of the concentration of the analyte.

Electronic biotransducers may be based on field-effect transistors (FETs). A FET is a type of transistor that uses an electric field to control the conductivity of a channel (e.g., a region depleted of charge carriers) between two electrodes (e.g., the source and drain) in a semiconducting material. Control of the conductivity of the channel may be achieved by varying the electric field potential, relative to the source and drain electrode, at a third electrode, known as the gate. Depending on the configuration and doping of the semiconducting material, the presence of a sufficient positive or negative potential at the gate electrode can either attract charge carriers (e.g., electrons) or repel charge carriers in the conduction channel resulting in a change in drain current. Accordingly, as a target analyte accumulates on the gate electrode, a change in drain current can be determined and compared to a reference electrode to determine an analyte level or concentration.

Examples of various types of electrodes discussed herein are exemplary and do not provide an exhaustive list of electrodes that may be used in the apparatus, systems, and methods described herein. In general, the apparatus, systems, and methods described herein include at least one working electrode (e.g., an electrode sensitive to a target analyte) and at least two different reference electrodes (e.g., electrodes that are not sensitive to the target analyte). Signals from working electrodes may be compared to one or more refence baselines derived from baseline signals provided by the reference electrodes to determine the portion of the signals from the working electrodes that corresponds to the analyte level or concentration of the target environment (e.g., target environment 10). However, reference electrodes may be subject to noise, drift, or other error conditions that can impact the accuracy of sensor output results (e.g., analyte levels or concentration). To correct for drift or other error conditions such as noise, apparatus, systems, and methods described herein may utilize at least two different reference electrodes.

The plurality of electrodes 106 include one or more working electrodes 110, a first reference electrode 112, and a second reference electrode 114. The one or more working electrodes 110 may each provide an analyte signal based on a presence of the analyte in the target environment 10. The one or more working electrodes 110 may be configured to interact with the analyte in such a way that the provided analyte signals vary in proportion to the concentration of the analyte in the target environment 10. For example, the one or more working electrodes 110 may include a bioreceptor that causes molecules of the analyte to accumulate on the one or more working electrodes 110 in proportion to the concentration of the analyte in the target environment 10. Accordingly, the analyte signals may vary in proportion to the concentration of the analyte in the target environment 10.

The reference electrodes 112, 114 may each provide a baseline signal of the target environment 10. The first reference electrode 112 may be configured to provide a first baseline signal of the target environment. Additionally, the second reference electrode 114 may be configured to provide a second baseline signal of the target environment. In general, the reference electrodes 112, 114 do not react to the analyte. In other words, the baseline signals provided by the reference electrodes 112, 114 are unaffected by the presence of the analyte in the target environment 10. Instead, the baseline signals may be representative of noise, electrode dissolution, electrode degradation, electrode reactions in the target environment, and other conditions of the target environment 10 that may impact signals provided by any of the plurality of electrodes 106.

The second reference electrode 114 may be a different type of electrode than the first reference electrode 112. As used herein, an "electrode type" or "type of electrode" may refer the physical and/or chemical characteristics of a particular electrode. In other words, electrodes of the same type may generally have the same nominal physical and/or chemical characteristics. In contrast, electrodes of a different type from one another may have one or more nominal characteristics that are different. Such different physical and/or chemical characteristics may cause the first baseline signal and the second baseline signal (e.g., measured values) to differ from each other and/or differ from the actual values the baseline signals are meant to represent in predictable ways. Such differences in the baseline signal may be leveraged to provide a more accurate measurements of the analyte in the target environment.

Figure 3:
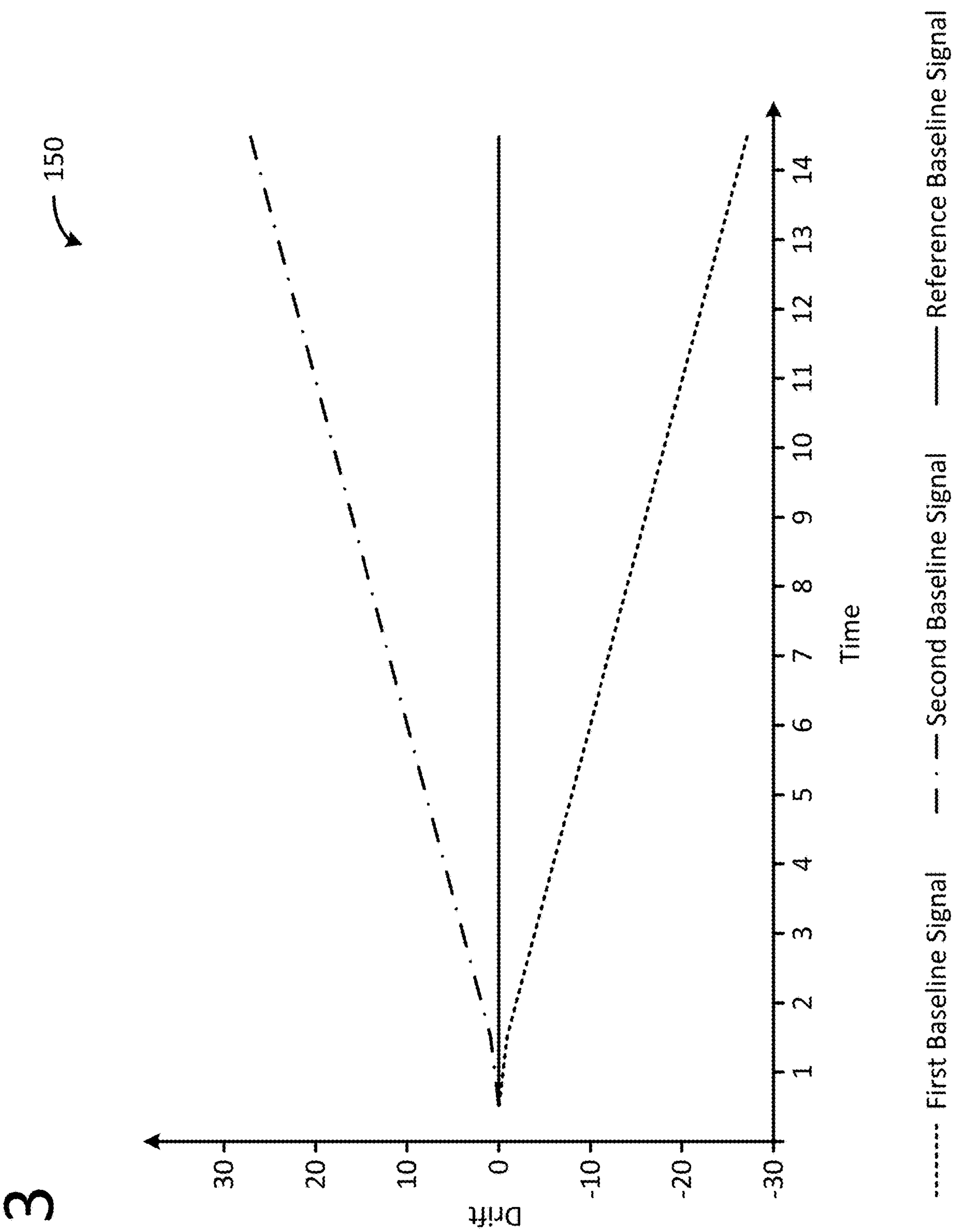
FIG. 3 is a graph depicting an example of signal drift over time.

In one or more embodiments, the first reference electrode 112 may be configured to have a positive drift in the target environment 10 and the second electrode 114 may be configured to have a negative drift in the target environment 10. In general, drift refers to changes in measurement error over time. An example of signal drift exhibited by a sensor apparatus that includes reference electrodes with positive and negative drift configurations is shown by a graph 150 depicted in FIG. 3. As shown in FIG. 3, the drift of the first baseline signal is shown by the dashed dot line, the drift of the second baseline signal is shown by the dotted line, and the drift of the reference baseline signal is shown by the solid line.

The drift of the first baseline signal, as shown by the graph 150, is an example of the drift or measurement error of an electrode (e.g., the first reference electrode 112) configured to have a positive drift or bias in the target environment (e.g., target environment 10). As can be seen in the graph 150, the drift of the first baseline signal increases in the positive direction over time. Accordingly, the first baseline signal will be representative of a value that is greater than an actual value of a parameter the first electrode 112 is configured to detect. Conversely, the drift of the second baseline signal, as shown by graph 150, is an example of the drift or measurement error of an electrode (e.g., the second reference electrode 114) configured to have a negative drift or bias in the target environment (e.g., target environment 10). As can be seen in the graph 150, the drift of the second baseline signal increases in the negative direction over time. Accordingly, the second baseline signal will be representative of a value that is less than an actual value of a parameter the second electrode 114 is configured to detect. Thus, when using electrodes that drift in different directions in a predictable manner (e.g., an electrode with a positive drift and an electrode with a negative drift), the baseline signals provided by such electrodes may be used to provide a reference baseline signal with drift correction.

To provide drift or other error correction, a reference baseline may be determined, or a reference baseline signal may be provided, based on the first baseline signal and the second baseline signal. The reference baseline may be a value that can be represented by a baseline signal. The reference baseline or the reference baseline signal may be used to determine or provide an analyte level that accounts for electrode drift, noise, or other sources of measurement error. The reference baseline may be determined by averaging the first baseline signal and the second baseline signal. In other words, the reference baseline may be the average of the values represented by the first baseline signal and the second baseline signal. The baseline reference signal may be provided based on the reference baseline. Alternatively, reference baseline signal may be provided by averaging the first baseline signal and the second baseline signal. The first baseline signal and second baseline signal may be averaged using hardware and/or software.

An example of the drift of a reference baseline signal determined or provided by the average of the first baseline signal and the second baseline signal is depicted by graph 150. The reference baseline signal, as shown in graph 150, does not drift over time because the drift of the first baseline signal is inversely proportional to the drift of the second baseline signal. In other words, the drift of the first baseline signal increases in the positive direction at the same rate the drift of the second baseline signal increases in the negative direction. Accordingly, when an average of the first baseline signal and the second baseline signal is taken, the drift of each sensor may be corrected. In other words, the drift of the first baseline signal and the drift of the second baseline signal may be diminished or removed entirely.

However, in real world conditions, the rate of drift of each of the reference electrodes 112, 114 may differ to some degree. While drift may not be removed entirely when the rate of drift of the reference electrodes 112, 114 differs, the magnitude of the drift of the reference baseline or reference baseline signal may generally be less than the magnitude of the drift of either of the reference electrodes 112, 114 taken alone. The magnitude of drift of the reference baseline signal may be less because the drift of the reference baseline signal is equal to the average of a positive drift (e.g., the drift of the first baseline signal) and a negative drift (e.g., the drift of the second baseline signal). Accordingly, the sum of the positive drift and the negative drift will have a magnitude less than at least one of the positive drift and the negative drift and the average will be half the magnitude of the sum. This relationship holds true even if additional pairs of reference electrodes are added as shown by Equation 1 below.

$$RBD = \frac{BD_1 + BD_2 + \ldots\ BD_n}{n} \qquad \text{(Equation 1)}$$

As shown in Equation 1, the drift of the reference baseline (RBD) is equal to the sum of each of the drifts of the baseline signals (BD) provided by the reference electrodes. In general, the number (n) of reference electrodes and their corresponding baseline signals may be even to allow for an equal number of electrodes configured to have a positive drift and electrodes configured to have a negative drift. Accordingly, when the reference electrodes are configured to have generally similar rates of drift in the target environment, the sum of the drifts of the baseline signals will be closer to zero. Furthermore, as the number of reference electrodes increases, the average of the drifts also becomes closer to zero. Thus, the use of pairs of reference electrodes having opposite drift biases in the target environment may allow for more stable and error free reference baseline signals to be provided. Additionally, increasing the number of reference electrode pairs having opposite drift biases in the target environment may further reduce the drift of the reference baseline or reference baseline signal.

The reference baseline may be determined, or the reference baseline signal may be provided, based on the first baseline signal and the second base line signal using other techniques as well. For example, the reference baseline may be determined by summing, subtracting, or otherwise combining the first and second reference signals. The reference baseline may also be determined using weighted combinations of the baseline signals provided by the reference electrodes as shown in Equation 2 below.

$$RBD = \frac{BD_1}{x} + \frac{BD_1}{y} + \ldots\ \frac{BD_n}{z} \qquad \text{(Equation 2)}$$

As shown in Equation 2, the drift of the reference baseline (RBD) is equal to the sum of weighted drifts of each of the baseline signals (BD) provided by the reference electrodes. The weight given to each electrode or baseline signal can be assigned or adjusted as represented by the denominators x, y, and z. By weighting the drifts or electrode signals, the number (n) of reference electrodes and their corresponding baseline signals may be odd or even because the balance of electrodes that have a positive drift and a negative drift can be accounted for in the way the baseline signals are weighted.

The sensor apparatus 102 may optionally include other electrodes in addition to any working electrodes 110 or the reference electrodes 112, 114. For example, the sensor apparatus 102 may include a counter electrode 116. Generally, a counter electrode may refer to an element used as a current path to complete a circuit of an analyte sensor apparatus that uses current flow between electrodes to sense an analyte. For example, the counter electrode may be used for cyclic voltammetry, linear sweep voltammetry, and other electrochemical techniques. The counter electrode may be operatively coupled to a power supply to provide a voltage or current within the target environment 10 or to other components of the analyte sensor apparatus 102. Accordingly, power supplied to the plurality of electrodes 106 may be reduced. Similarly, a reduction in power requirements may allow a reduction in the size of the plurality of electrodes 106. Such voltage or current may be supplied primarily by the counter electrode 116 instead of the working electrodes 110 or the reference electrodes 112, 114.

In one or more embodiments, the sensor apparatus 102 may include the counter electrode 116 configured to provide a current in the target environment 10 and the second reference electrode 114 may include an open circuit potential electrode. In such a configuration, amperometric sensing may be provided using the working electrode 110, the first reference electrode 112, and the counter electrode 116. In general, a change in potential between the first reference electrode 112 and the second reference electrode 114 may be proportional to an ion concentration in the target environment.

Furthermore, the sensor apparatus may optionally include one or more other additional electrodes 118. The one or more electrodes 118 may include any suitable electrode to provide noise, drift, or other error correction. The electrode 118 may include a blank electrode. A blank electrode may be an electrode that responds to background noise of the target environment 10 but does not otherwise react (chemically or otherwise) to the target environment. Error correction signals provided by blank electrodes may be used to correct for background noise that may affect reference electrodes 112, 114.

The analyte sensor apparatus 102 may also include a controller 120 operatively coupled to the plurality of electrodes 106. The controller may be configured to receive the first baseline signal and the second baseline signal provided by the reference electrodes 112, 114 and the analyte signals provided by the working electrode 110. The controller 120 may receive signals from the plurality of electrodes 106 via any suitable wired or wireless connection.

The controller 120 may further be configured to provide one or more analyte levels based on the baseline signal and the one or more analyte signals. The one or more analyte levels may be provided or determined based on a difference between the baseline signal and each of the one or more analyte signals.

Still further, the controller 120 may be configured to provide an error correction factor based on the baseline signal and the at least one error correction signal. The error correction factor may be provided or determined based on a difference between the baseline signal and the at least one error correction signal. Additionally, or alternatively, the error correction factor may be provided or determined based on any subtraction or differential method such as digital signal processing, noise subtraction, blind spot suppression, etc.

The controller 120 may further be configured to output one or more adjusted analyte levels based on the one or more analyte levels and the at least one error correction factor. Each of the one or more adjusted analyte levels may be a difference between an analyte level and the at least one error correction factor. In some embodiments, each of the one or more adjusted analyte levels are output by a difference amplifier that receives a provided analyte level and at least one error correction factor as inputs. In some embodiments, the controller 120 may determine the one or more adjusted analyte levels (e.g., using digital logic, one or more processors, etc.) based on the one or more analyte levels and the at least one error correction factor.

In some embodiments, the controller 120 may be an analog controller that includes one or more resistors, capacitors, operational amplifiers, comparators, filters, differential amplifiers, or other analog circuitry to provide various outputs without the use of digital circuitry, digital logic, or a processor. Such analog controller may be configured to provide one or more analyte levels based on the baseline signal and the one or more analyte signals. For example, a differential amplifier may provide a signal representative of the analyte level by providing the difference between an analyte signal and the baseline signal. Additional analogue circuitry may be used to provide the error correction factor and output the adjusted analyte levels.

In some embodiments, the controller 120 may additionally or alternatively include one or more processors, logic gates, or other digital circuitry to determine analyte levels and reference baselines. The controller 120 may include data storage for data storage and access to processing programs or routines that may be employed to carry out the techniques, processes, and algorithms for detecting an analyte in a target environment. For example, processing programs or routines may include programs or routines for determining one or more analyte levels, determining reference baselines, determining adjusted analyte levels, filtering background noise, computational mathematics, matrix mathematics, Fourier transforms, compression algorithms, calibration algorithms, inversion algorithms, signal processing algorithms, normalizing algorithms, deconvolution algorithms, averaging algorithms, standardization algorithms, comparison algorithms, vector mathematics, or any other processing required to implement one or more embodiments as described herein.

The analyte sensor apparatus 102 may also include a communication interface 122 to communicate with one or more external devices. The communication interface 122 may include any suitable hardware or devices to provide wired or wireless communication with the one or more external devices. For example, the communication interface 122 may include one or more of a receiver, transmitter, transceiver, ethernet port, Universal Serial Bus (USB) port, cables, controller, or other device to facilitate wired or wireless communication. The communication interface 122 may facilitate communication using any suitable protocol or protocols. For example, the communication interface 122 may utilize Ethernet, Recommended Standard 232, Universal Asynchronous Receiver Transmitter or Universal Synchronous Asynchronous Receiver Transmitter (UART/USART), USB, BLUETOOTH, Wi-Fi, Near Field Communication (NCF), etc. The communication interface 122 may allow communication between the analyte sensor apparatus 102 and a computing apparatus such as the computing apparatus 104.

The system 100 may also include the computing apparatus 104. The computing apparatus 104 may be, for example, any fixed or mobile computer system (e.g., a personal computer, a tablet computer, a mobile device, a cellular phone, a wearable device, etc.). The exact configuration of the computing apparatus 104 is not limiting and essentially any device capable of providing suitable computing capabilities and control capabilities (e.g., control analyte sensing of the analyte sensor apparatus 102, the acquisition of data such as sensor data, determination of various parameters such as analyte levels, error correction factors, adjusted analyte levels, etc.) may be used. Further, various peripheral devices, such as a computer display, mouse, keyboard, memory, printer, scanner, etc. are contemplated to be used in combination with the computing apparatus 104.

The computing apparatus 104 may be operatively coupled to the analyte sensor apparatus 102. For example, the computing apparatus 104 may be operatively coupled to the analyte sensor apparatus 102 via analog electrical connections, digital electrical connections, wireless connections, bus-based connections, network-based connections, internet-based connections, etc. The computing apparatus 104 can transmit data to and receive data from the analyte sensor apparatus 102. Data received from the analyte sensor apparatus 102 may include, for example, analyte signals, baseline signals, reference baseline signals, analyte levels, error correction factors, adjusted analyte levels, biotransducer status information, sensor parameters, etc. The computing apparatus 104 may be configured execute processes and methods described herein using data received from the analyte sensor apparatus 102. For example, the computing apparatus may be configured to determine analyte levels, reference baselines, correction factors, adjusted analyte levels, etc. Data transmitted by the computing apparatus 104 to the analyte sensor apparatus 102 may include commands, sensor settings, thresholds, parameters, etc.

Additionally, the analyte sensor apparatus 102 and the computing apparatus 104 may each include display apparatus 130, 134, respectively, that may be configured to display data. For example, the display apparatus 130, 134 may be configured to display one or more of the analyte levels, reference baselines, error correction factors, adjusted analyte levels, biotransducer status information, sensor parameters, etc. The display apparatus 130, 134 may include any apparatus capable of displaying information to a user, such as a graphical user interface 132, 136 including one or more metrics indicative of medical system therapy (e.g., cardiac conduction system therapy, neurostimulation, etc.) benefit, one or more metrics indicative of analyte signals, baseline signals, reference baseline signals, error correction signals, analyte levels, error correction factors, adjusted analyte levels, biotransducer status information, sensor parameters, textual instructions, graphical depictions the target environment, graphical depictions or actual images of the plurality of electrodes 106, etc. Further, the display apparatus 130, 134 may include a liquid crystal display, an organic light-emitting diode screen, a touchscreen, a cathode ray tube display, etc.

A schematic block diagram of another analyte sensing system 200 according to embodiments described herein is shown in FIG. 3. The analyte sensing system 200 may include a computing apparatus or processor 202 and a plurality of electrodes 209. Generally, the plurality of electrodes 209 may be operatively coupled to the computing apparatus 202 and may include any suitable circuits or devices configured to provide signals for detecting an analyte in a target environment (e.g., baseline signals, analyte signals, and error condition signals) similar to the plurality of electrodes 106 of FIGS. 1 and 2.

The plurality of electrodes 209 includes one or more working electrodes 210, a first reference electrode 212, and a second reference electrode 214. The one or more working electrodes 210 are configured to provide an analyte signal based on the presence of the analyte in the target environment and may include any of the features described herein with regard to working electrode 110. The first reference electrode 212 is configured to provide a first baseline signal of the target environment and may include any of the features described herein with regard to reference electrode 112. The second reference electrode 214 is configured to provide a second baseline signal of the target environment and may include any of the features described herein with regard to the second reference electrode 212.

The analyte sensing system 200 may optionally include a counter electrode 216. The first reference electrode 212 may be operatively coupled to the counter electrode 216. The counter electrode 216 may be configured to provide power to the plurality of electrodes 209 and may include any of the features described herein with regard to counter electrode 116. The analyte sensing system 200 may optionally include one or more electrodes 218. The one or more electrodes 218 may include any of the features described herein with regard to the electrode 118. For example, the one or more electrodes 218 may include a blank electrode.

Further, the computing apparatus 202 includes data storage 204. Data storage 204 allows for access to processing programs or routines 206 and one or more other types of data 208 that may be employed to carry out the techniques, processes, and algorithms for charging a battery or one or more electrochemical cells. For example, processing programs or routines 206 may include programs or routines for providing/determining analyte levels, providing/determining reference baselines, providing/determining error correction factors, outputting/determining adjusted analyte levels, filtering background noise, transmitting data, receiving data, determining thresholds, computational mathematics, matrix mathematics, Fourier transforms, compression algorithms, calibration algorithms, image construction algorithms, inversion algorithms, signal processing algorithms, normalizing algorithms, deconvolution algorithms, averaging algorithms, standardization algorithms, comparison algorithms, vector mathematics, or any other processing required to implement one or more embodiments as described herein.

Data 208 may include, for example, signal data, analyte level data, baseline data, reference baseline data, error correction factor data, biotransducer settings/parameters, calibration data, resistance calculations, device settings, error bit states, historical data, thresholds, arrays, meshes, grids, variables, counters, statistical estimations of accuracy of results, results from one or more processing programs or routines employed according to the disclosure herein (e.g., detecting an analyte in a target environment, determining adjusted analyte levels, etc.), or any other data that may be necessary for carrying out the one or more processes or techniques described herein.

In one or more embodiments, the analyte sensing system 200 may be controlled using one or more computer programs executed on programmable computers, such as computers that include, for example, processing capabilities (e.g., microcontrollers, programmable logic devices, etc.), data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or processes as described herein or as would be applied in a known fashion.

The programs used to implement the processes described herein may be provided using any programmable language, e.g., a high-level procedural and/or object orientated programming language that is suitable for communicating with a computer system. Any such programs may, for example, be stored on any suitable device, e.g., a storage media, readable by a general or special purpose program, computer or a processor apparatus for configuring and operating the computer when the suitable device is read for performing the procedures described herein. In other words, at least in one embodiment, the analyte sensing system 200 may be controlled using a computer readable storage medium, configured with a computer program, where the storage medium so configured causes the computer to operate in a specific and predefined manner to perform functions described herein.

The computing apparatus 202 may be, for example, any fixed or mobile computer system (e.g., a personal computer or minicomputer). The exact configuration of the computing apparatus is not limiting and essentially any device capable of providing suitable computing capabilities and control capabilities (e.g., control electrode output such as voltage, current, photon, or other sensing outputs; the acquisition of data, such as sensor data; etc.) may be used. Additionally, the computing apparatus 202 may be incorporated in a housing of the analyte sensing system 200. Further, various peripheral devices, such as a computer display, mouse, keyboard, memory, printer, scanner, etc. are contemplated to be used in combination with the computing apparatus 202. Further, in one or more embodiments, the data 208 (e.g., signal data, analyte level data, baseline data, reference baseline data, error correction factor data, biotransducer settings/parameters, calibration data, etc.) may be analyzed by a user, used by another machine that provides output based thereon, etc. As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by computing apparatus 202 described herein. Also, as described herein, a file in user-readable format may be any representation of data (e.g., ASCII text, binary numbers, hexadecimal numbers, decimal numbers, audio, graphical) presentable on any medium (e.g., paper, a display, sound waves, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware that is to be used to implement the processes described herein shall not be limiting on the scope of the systems, processes or programs (e.g., the functionality provided by such systems, processes or programs) described herein.

The techniques described in this disclosure, including those attributed to the systems, or various constituent components, may be implemented, at least in part, in hardware, software, firmware, or any combination thereof. For example, various aspects of the techniques may be implemented by the computing apparatus 202, which may use one or more processors such as, e.g., one or more microprocessors, DSPs, ASICs, FPGAs, CPLDs, microcontrollers, or any other equivalent integrated or discrete logic circuitry, as well as any combinations of such components, image processing devices, or other devices. The term "processing apparatus," "processor," or "processing circuitry" may generally refer to any of the foregoing logic circuitry, alone or in combination with other logic circuitry, or any other equivalent circuitry. Additionally, the use of the word "processor" may not be limited to the use of a single processor but is intended to connote that at least one processor may be used to perform the techniques and processes described herein.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by the computing apparatus 202 to support one or more aspects of the functionality described in this disclosure.

Figure 4:
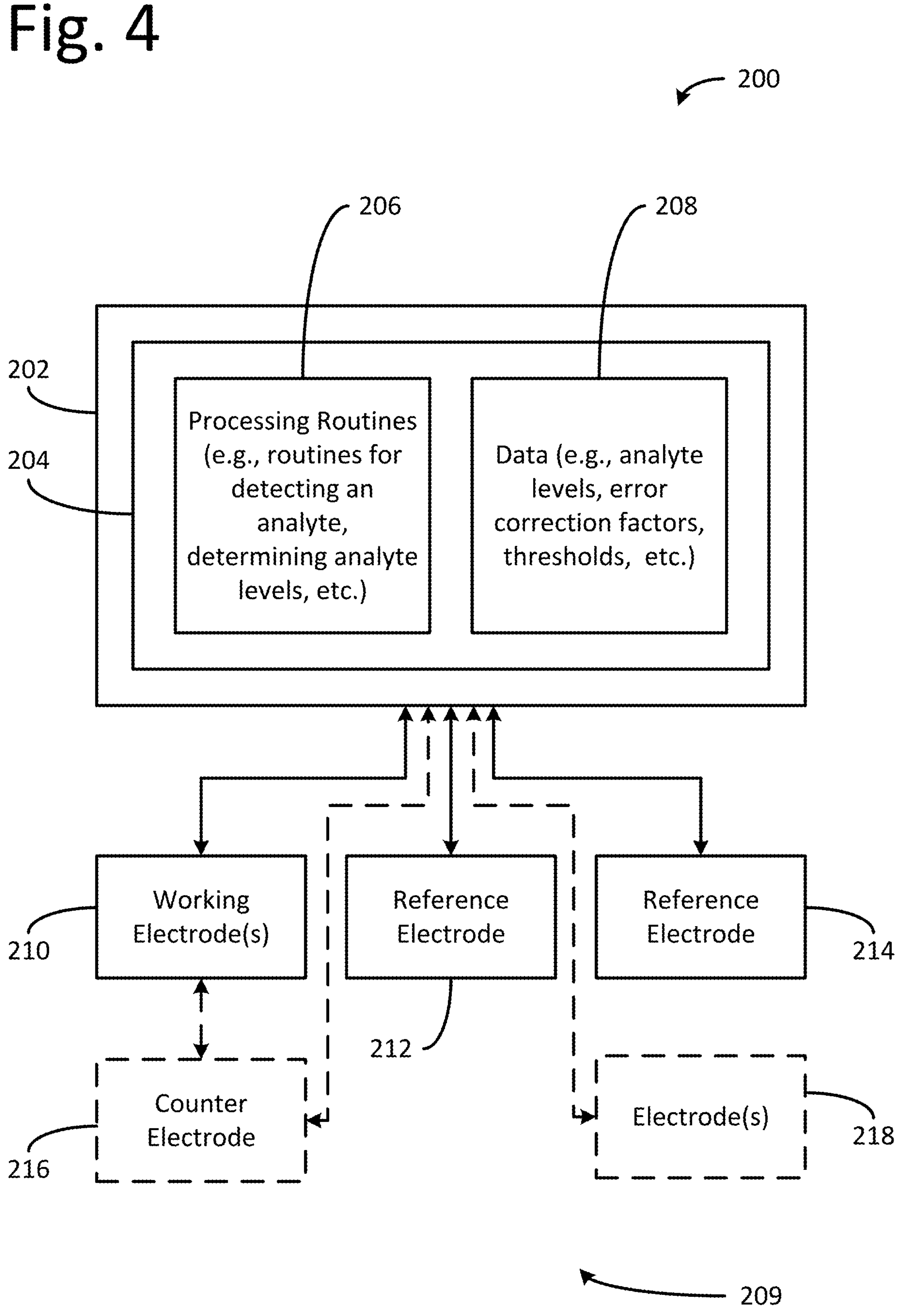
FIG. 4 is a schematic block diagram another embodiment of an analyte sensing system.
Figure 5:
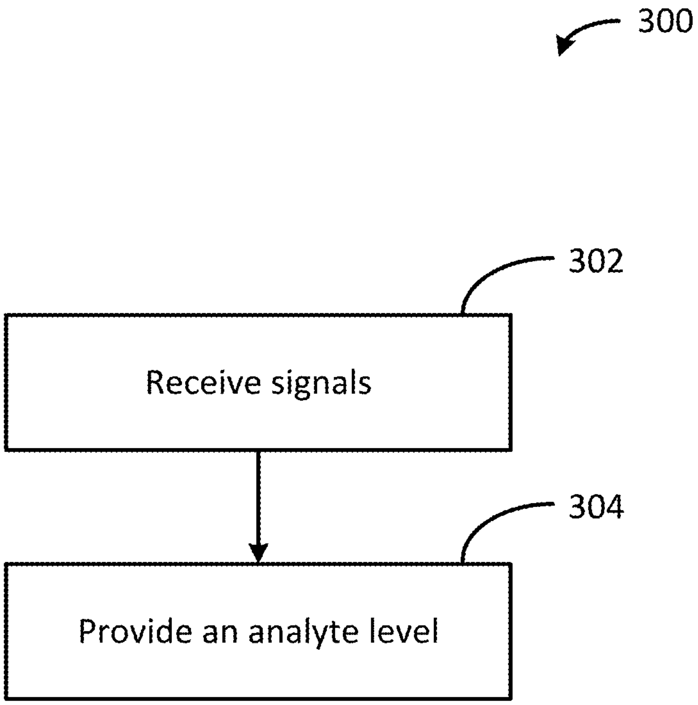
FIG. 5 is a flow diagram of an embodiment of a process for detecting an analyte in a target environment.

A method or process 300 of detecting an analyte in a target environment is shown in FIG. 5. Although described in regard to analyte sensor apparatus 102 of FIGS. 1 and 2 or analyte sensing system 200 of FIG. 4, the method 300 may be carried out using any suitable analyte sensing apparatus or system.

The method 300 may include receiving a plurality of electrode signals 302. The plurality of electrode signals may include one or more analyte signals of the target environment (e.g., target environment 10) from one or more working electrodes (e.g., working electrode 110 or 210) disposed in the target environment, a first baseline signal of the target environment from a first reference electrode (e.g., first reference electrode 112 or 212) and a second baseline signal of the target environment from a second electrode (e.g., second reference electrode 114 or 214). The second electrode may include a different type of electrode than the first electrode.

In one or more embodiments, the first reference electrode may be configured to have a negative drift in the target environment and the second reference electrode may be configured to have a positive drift in the target environment. In one or more embodiments, the second reference electrode may include an open circuit potential electrode. Additionally, amperometric sensing may be provided using the one or more working electrodes, the first reference electrode, and a counter electrode (e.g., counter electrode 116 or 216). Amperometric sensing may also be provided using the one or more working electrodes, a reference baseline signal (e.g., a sum, average, or difference of the baseline signals), and a counter electrode (e.g., counter electrode 116 or 216). In one or more embodiments, the second reference electrode may be an ion selective electrode.

In one or more embodiments, the plurality of electrode signals further includes signals from one or more additional electrodes (e.g., electrode 118 or 218). The plurality of electrode signals may include a blank baseline signal provided by a blank electrode. The plurality of electrode signals may include an error correction signal provided by a working as reference electrode.

The method 300 may further include providing one or more analyte levels based on the plurality of electrode signals 304. The analyte level may be provided by a sensing apparatus or a computing apparatus. In one or more embodiments, the analyte level may be provided by the sensing apparatus as a signal representative of the analyte level (e.g., an analyte level signal). The analyte level signal may be provided using a communication interface (e.g., communication interface 122). The analyte level signal may be a wired or wireless signal. In one or more embodiments, the analyte signal may be provided by a display (e.g., displays 130, 134). Additionally, providing the analyte level may include displaying the one or more adjusted analyte levels. Displaying the one or more adjusted analyte levels may include displaying the one or more adjusted analyte levels on at least one of the display apparatus (e.g., display apparatus 130 or 134) and/or graphical user interfaces (e.g., graphical user interface 132 or 136). The one or more adjusted analyte levels may be displayed as a number, graph, or other visual representation of the adjusted analyte levels.

To provide the one or more analyte levels, the method 300 may further include determining a reference baseline or providing a reference baseline signal. A reference baseline may be determined based on the first baseline signal and the second baseline signal, and an analyte level may be determined based on the analyte signal and the reference baseline. The reference baseline may be an average baseline. In other words, the reference baseline may be an average of baseline signals provided by reference electrodes (e.g., the reference electrodes 112, 114) of the sensor apparatus. An average baseline may be determined based on the first baseline signal and the second baseline signal, and the analyte level may be determined based on the analyte signal and the average baseline. A reference baseline signal may be provided by averaging the first baseline signal and the second baseline signal and at least one sensor signal representative of the analyte level of the target environment may be provided based on the analyte signal and the reference baseline signal. The reference baseline may also be a summation, difference, or other combination of the baseline signals.

Determining a reference baseline or providing a reference baseline signal may also include one or more additional techniques to allow noise and other errors to be removed from the one or more analyte signals to provide or determine a more accurate analyte level. The differences between the one or more analyte signals and an actual analyte level in the target environment may be caused by electrical noise, magnetic noise, light induced artifacts, movement induced artifacts, non-faradaic currents, faradaic non-analyte induced currents, background environment conductivity, or electrochemical drift. In some embodiments, providing the analyte level may include providing the result of any suitable subtraction or differentiation method applied to the one or more analyte signals and the reference baseline signals such as, for example, digital signal processing, noise subtraction, blind spot suppression, etc.

The invention is defined in the claims. However, below there is provided a non-exhaustive list of non-limiting examples. Any one or more of the features of these examples may be combined with any one or more features of another example, embodiment, or aspect described herein.

Example Ex1: A sensor apparatus comprising: a plurality of electrodes to provide a plurality of electrode signals based on a target environment, the plurality of electrodes comprising: one or more working electrodes configured to provide an analyte signal based on a presence of an analyte in the target environment; a first reference electrode configured to provide a first baseline signal of the target environment; and a second reference electrode comprising a different type of electrode than the first reference electrode, the second reference electrode configured to provide a second baseline signal of the target environment; a controller operatively coupled to the plurality of electrodes and configured to: receive the plurality of electrode signals, the plurality of electrode signals comprising the analyte signal, the first baseline signal, and the second baseline signal; and provide one or more sensor signals based on the received plurality of electrode signals.

Example Ex2: The apparatus as in example Ex1, wherein the controller is further configured to provide at least one sensor signal representative of an analyte level of the target environment using the received plurality of electrode signals, and wherein the one or more sensor signals comprises the sensor signal that is representative of the analyte level.

Example Ex3: The apparatus as in example Ex1, wherein the controller comprises one or more processors and is further configured to: determine a reference baseline based on the first baseline signal and the second baseline signal; and determine an analyte level of the target environment based on the analyte signal and the reference baseline.

Example Ex4: The apparatus as in example Ex1, wherein the controller is further configured to: determine an average baseline based on the first baseline signal and the second baseline signal; and determine an analyte level of the target environment based on the analyte signal and the average baseline signal and wherein the one or more sensor signals comprises a signal representative of the analyte level.

Example Ex5: The apparatus as in example Ex1, wherein the controller is further configured to: provide a reference baseline signal by averaging the first baseline signal and the second baseline signal; and provide at least one sensor signal representative of an analyte level of the target environment based on the analyte signal and the reference baseline signal.

Example Ex6: The apparatus as in example Ex1, wherein the first reference electrode is configured to have a negative drift in the target environment and the second reference electrode is configured to have a positive drift in the target environment.

Example Ex7: The apparatus as in example Ex1, further comprising a counter electrode configured to provide a current in the target environment, wherein the second reference electrode comprises an open circuit potential electrode, and wherein the controller is further configured to provide amperometric sensing using the working electrode, the first reference electrode, and the counter electrode.

Example Ex8: The apparatus as in example Ex1, further comprising a counter electrode configured to provide a current in the target environment and wherein the second reference electrode comprises an ion selective electrode.

Example Ex9: The apparatus as in example Ex1, wherein the analyte sensor apparatus comprises a communication interface configured to transmit the one or more sensor signals to an external device.

Example Ex10: The apparatus as in example Ex1, wherein the analyte sensor apparatus comprises an implantable medical device.

Example Ex11: An analyte sensing system comprising: a sensor apparatus to provide one or more sensor signals based on a plurality of electrode signals, the sensor apparatus comprising: a plurality of electrodes to provide the plurality of electrode signals based on a target environment, the plurality of electrodes comprising: one or more working electrodes configured to provide an analyte signal based on a presence of an analyte in the target environment; a first reference electrode configured to provide a first baseline signal of the target environment; and a second reference electrode comprising a different type of electrode than the first reference electrode, the second reference electrode configured to provide a second baseline signal of the target environment; the plurality of electrode signals comprising the analyte signal, the first baseline signal, and the second baseline signal; and a computing apparatus comprising one or more processors and operatively coupled to the sensor apparatus, the computing apparatus configured to: receive the one or more sensor signals; and provide an analyte level of the target environment based on the one or more sensor signals.

Example Ex12: The system as in example Ex11, wherein the sensor apparatus comprises a controller configured to provide the one or more sensor signals using the received plurality of electrode signals and wherein the one or more sensor signals comprises at least one sensor signal representative of the analyte level.

Example Ex13: The system as in example Ex11, wherein the one or more sensor signals comprises: an analyte sensor signal corresponding to the analyte signal; a first baseline sensor signal corresponding to the first baseline signal; and a second baseline sensor signal corresponding to the second baseline signal; and wherein the computing apparatus is further configured to: determine a reference baseline based on the first baseline sensor signal and the second baseline sensor signal; and determine the analyte level of the target environment based on the analyte sensor signal and the reference baseline.

Example Ex14: The system as in example Ex11, wherein the one or more sensor signals comprises: an analyte sensor signal corresponding to the analyte signal; a first baseline sensor signal corresponding to the first baseline signal; and a second baseline sensor signal corresponding to the second baseline signal; and wherein the computing apparatus is further configured to: determine an average baseline based on the first baseline signal and the second baseline signal; and determine the analyte level based the average baseline and the analyte sensor signal.

Example Ex15: The system as in example Ex11, wherein the first reference electrode comprises an electrode configured to have a negative drift in the target environment and the second reference electrode is configured to have a positive drift in the target environment.

Example Ex16: The system as in example Ex11, wherein the sensor apparatus further comprises a counter electrode configured to provide a current in the target environment, wherein the second reference electrode comprises an open circuit potential electrode, and wherein the computing apparatus is further configured to provide amperometric sensing using the working electrode, the first reference electrode, and the counter electrode.

Example Ex17: The system as in example Ex11, further comprising a counter electrode configured to provide a current in the target environment and wherein the second reference electrode comprises an ion selective electrode.

Example Ex18: The system as in example Ex11, wherein the analyte sensor apparatus comprises an implantable medical device.

Example Ex19: The system as in example Ex11, wherein the sensor apparatus comprises a wearable device.

Example Ex20: The system as in example Ex11, wherein the sensor apparatus further comprises a communication interface configured to wirelessly transmit the one or more sensor signals to the computing apparatus.

Example Ex21: The system as in example Ex11, wherein the computing apparatus further comprises a display and wherein to provide the analyte level the computing apparatus is configured to display the analyte level using the display.

Example Ex22: A method for detecting an analyte in a target environment comprising: receiving a plurality of electrode signals, the plurality of electrode signals comprising: one or more analyte signals of the target environment from one or more working electrodes disposed in the target environment; a first baseline signal of the target environment from a first reference electrode; and a second baseline signal of the target environment from a second electrode, the second electrode comprising a different type of electrode than the first electrode; providing an analyte level of the target environment based on the plurality of electrode signals.

Example Ex23: The method as in example Ex22, further comprising: determining a reference baseline based on the first baseline signal and the second baseline signal; and determining an analyte level based on the analyte signal and the reference baseline.

Example Ex24: The method as in example Ex22, further comprising: determining an average baseline based on the first baseline signal and the second baseline signal; and determining the analyte level based on the analyte signal and the average baseline.

Example Ex25: The method as in example Ex22, further comprising: providing a reference baseline signal by averaging the first baseline signal and the second baseline signal; and providing at least one sensor signal representative of an analyte level of the target environment based on the analyte signal and the reference baseline signal.

Example Ex26: The method as in example Ex22, wherein the first reference electrode is configured to have a negative drift in the target environment and the second reference electrode is configured to have a positive drift in the target environment.

Example Ex27: The method as in example Ex22, wherein the second reference electrode comprises an open circuit potential electrode, the method further comprising providing amperometric sensing using the one or more working electrodes, the first reference electrode, and a counter electrode.

Example Ex28: The method as in example Ex22, wherein the second reference electrode comprises an ion selective electrode.

As used herein, singular forms "a," "an" and "the" include plural referents unless the context clearly dictates otherwise. As used in this specification and the appended claims, the term "or" is generally employed in its sense including "and/or" unless the content clearly dictates otherwise. The term "and/or" means one or all of the listed elements or a combination of any two or more of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the inventive technology.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

It will be apparent to those skilled in the art that various modifications and variations can be made to the present inventive technology without departing from the spirit and scope of the disclosure. Since modifications, combinations, sub-combinations and variations of the disclosed embodiments incorporating the spirit and substance of the inventive technology may occur to persons skilled in the art, the inventive technology should be construed to include everything within the scope of the appended claims and their equivalents.

What is claimed is:

1. A sensor apparatus comprising:

a plurality of electrodes to provide a plurality of electrode signals based on a target environment, the plurality of electrodes comprising:

one or more working electrodes configured to provide an analyte signal based on a presence of an analyte in the target environment;

a first reference electrode configured to provide a first baseline signal of the target environment, the first reference electrode having a negative drift in the target environment; and a second reference electrode comprising a different type of electrode than the first reference electrode, the second reference electrode configured to provide a second baseline signal of the target environment, the second reference electrode having a positive drift in the target environment; and a controller operatively coupled to the plurality of electrodes and configured to:

receive the plurality of electrode signals, the plurality of electrode signals comprising the analyte signal, the first baseline signal, and the second baseline signal;

determine a reference baseline signal based on a combination of the first baseline signal and the second baseline signal; and provide one or more sensor signals based on the one or more analyte signals and the determined reference baseline signal.

2. The apparatus as in claim 1, wherein the one or more sensor signals comprises at least one sensor signal that is representative of an analyte level of the target environment.

3. The apparatus as in claim 1, wherein the controller is further configured to:

determine the reference baseline signal by averaging the first baseline signal and the second baseline signal.

4. The apparatus as in claim 1, wherein the controller is further configured to:

determine the reference baseline signal by summing the first baseline signal and the second baseline signal.

5. The apparatus as in claim 1, further comprising a counter electrode configured to provide a current in the target environment, wherein the second reference electrode comprises an open circuit potential electrode, and wherein the controller is further configured to provide amperometric sensing using the working electrode, the first reference electrode, and the counter electrode.

6. The apparatus as in claim 1, wherein the sensor apparatus comprises an implantable medical device.

7. The apparatus as in claim 1, wherein the controller is further configured to determine the reference baseline signal by using a weighted combination of the first baseline signal and the second baseline signal.

8. The apparatus as in claim 1, wherein a rate of drift of the first reference electrode is inversely proportional with the rate of drift of the second reference electrode.

9. An analyte sensing system comprising:

a sensor apparatus to provide one or more sensor signals based on a plurality of electrode signals, the sensor apparatus comprising:

a plurality of electrodes to provide the plurality of electrode signals based on a target environment, the plurality of electrodes comprising:

one or more working electrodes configured to provide an analyte signal based on a presence of an analyte in the target environment;

a first reference electrode configured to provide a first baseline signal of the target environment, the first reference electrode having a negative drift in the target environment; and a second reference electrode comprising a different type of electrode than the first reference electrode, the second reference electrode configured to provide a second baseline signal of the target environment, the second reference electrode having a positive drift in the target environment;

the plurality of electrode signals comprising the analyte signal, the first baseline signal, and the second baseline signal; and a computing apparatus comprising one or more processors and operatively coupled to the sensor apparatus, the computing apparatus configured to:

receive the one or more sensor signals;

determine a reference baseline signal based on a combination of the first baseline signal and the second baseline signal; and provide an analyte level of the target environment based on the one or more sensor signals and the determined reference baseline signal.

10. The system as in claim 9, wherein the one or more sensor signals comprises at least one sensor signal that is representative of the analyte level of the target environment.

11. The system as in claim 9, wherein the one or more sensor signals comprises:

an analyte sensor signal corresponding to the analyte signal;

a first baseline sensor signal corresponding to the first baseline signal; and a second baseline sensor signal corresponding to the second baseline signal; and wherein the computing apparatus is further configured to:

determine the reference baseline signal by averaging the first baseline signal and the second baseline signal.

12. The system as in claim 9, wherein the sensor apparatus further comprises a counter electrode configured to provide a current in the target environment, wherein the second reference electrode comprises an open circuit potential electrode, and wherein the computing apparatus is further configured to provide amperometric sensing using the working electrode, the first reference electrode, and the counter electrode.

13. The system as in claim 9, wherein the sensor apparatus comprises an implantable medical device.

14. The system of claim 9, wherein the computing apparatus further comprises a display and wherein to provide the analyte level the computing apparatus is configured to display the analyte level using the display.

15. The analyte sensing system of claim 9, wherein the computing system is further configured to determine the reference baseline signal by using a weighted combination of the first baseline signal and the second baseline signal.

16. A method for detecting an analyte in a target environment comprising:

receiving a plurality of electrode signals, the plurality of electrode signals comprising:

one or more analyte signals of the target environment from one or more working electrodes disposed in the target environment;

a first baseline signal of the target environment from a first reference electrode, the first baseline signal having a negative drift in the target environment; and a second baseline signal of the target environment from a second electrode, the second electrode comprising a different type of electrode than the first electrode, the second baseline signal having a positive drift in the target environment;

determining a reference baseline signal based on a combination of the first baseline signal and the second baseline signal; and providing an analyte level of the target environment based on the one or more analyte signals and the determined reference baseline signal.

17. The method as in claim 16, further comprising:

determining the reference baseline signal by averaging the first baseline signal and the second baseline signal.

18. The method as in claim 16, further comprising:

determine the reference baseline signal by summing the first baseline signal and the second baseline signal.

19. The method of claim 16, further comprising determining the reference baseline signal by using a weighted combination of the first baseline signal and the second baseline signal.

* * * * *